US00PP33933P2

(12) United States Plant Patent
Bull

(10) Patent No.: US PP33,933 P2
(45) Date of Patent: Feb. 1, 2022

(54) ***RUDBECKIA* PLANT NAMED 'BULLRUDI 11'**

(50) Latin Name: ***Rudbeckia hirta* L.**
Varietal Denomination: BullRudi 11

(71) Applicant: Hartwig Bull, Gönnebek (DE)

(72) Inventor: Hartwig Bull, Gönnebek (DE)

(73) Assignee: Hartwig Bull, Gönnebek (DE)

( * ) Notice: Subject to any disclaimer, the term of this patent is extended or adjusted under 35 U.S.C. 154(b) by 0 days.

(21) Appl. No.: 17/400,459

(22) Filed: Aug. 12, 2021

Related U.S. Application Data

(60) Provisional application No. 63/103,641, filed on Aug. 14, 2020.

(51) Int. Cl.
*A01H 6/14* (2018.01)
*A01H 5/02* (2018.01)

(52) U.S. Cl.
USPC ..... Plt./474

(58) Field of Classification Search
USPC ..... Plt./474
See application file for complete search history.

*Primary Examiner* — Annette H Para
(74) *Attorney, Agent, or Firm* — The Webb Law Firm

(57) ABSTRACT

A new and distinct variety of *Rudbeckia* plant having a compact growth habit and large, rich yellow and reddish brown blooms with a dark brown center.

3 Drawing Sheets

Botanical classification: *Rudbeckia hirta* L.
Varietal denomination: 'BullRudi 11'.

BACKGROUND OF THE INVENTION

The present invention comprises a new and distinct cultivar of *Rudbeckia* plant known by the varietal name 'BullRudi 11'. The new variety was discovered in August of 2017 in Gönnebeck, Germany as the result of a planned breeding program with the purposes of providing *Rudbeckia* plants with improved growth, more uniformity, a compact growth habit, better branching, attractive foliage, large blooms, and unique flower colors. The new variety is the result of a cross between an unpatented *Rudbeckia hirta* L. variety having an internal breeder's reference of "BR 98-2014" (female parent) and an unpatented *Rudbeckia hirta* L. variety having an internal breeder's reference of "BR 201-2014" (male parent) from the breeder's own collection. The new variety was first asexually reproduced via in-vitro tissue culture cuttings in Gönnebek, Germany in September of 2017. The new variety is similar to its parental varieties in botanical classification, but exhibits bigger flowers, increased branching, and more attractive foliage than both of its parental varieties. Further, 'BullRudi 11' exhibits a different flower center color than its female parent and differs in its bicolored flowers and growth habit from its male parent.

When 'BullRudi 11' is compared to *Rudbeckia hirta* L. variety named 'Prairie Sun' (unpatented), 'BullRudi 11' is similar to 'Prairie Sun' in botanical classification, but 'BullRudi 11' exhibits improved plant quality, more uniform growth with increased self-branching, more attractive foliage, and large, bicolored blooms that distinguish it from 'Prairie Sun'. Further, the following characteristics distinguish 'BullRudi 11' when generally compared to other *Rudbeckia* varieties known to the breeder:

Large, bicolored blooms with a brown center;
Good self-branching;
An upright, compact, and uniform growth habit;
Healthy, green foliage;

Long bloom time;
Ease of growth; and
Unique flower color.

The new variety has been trial and field tested and has been found to retain its distinctive characteristics and remain true to type through successive asexual propagations. The present invention has not been evaluated under all possible environmental conditions. The phenotype may vary with variations in environment without a change in the genotype of the plant.

DESCRIPTION OF THE DRAWINGS

The accompanying photographic drawings illustrate the new variety at 18 weeks of age, with the color being as nearly true as is possible with color illustrations of this type.

DESCRIPTION OF THE PLANT

Figure 1:
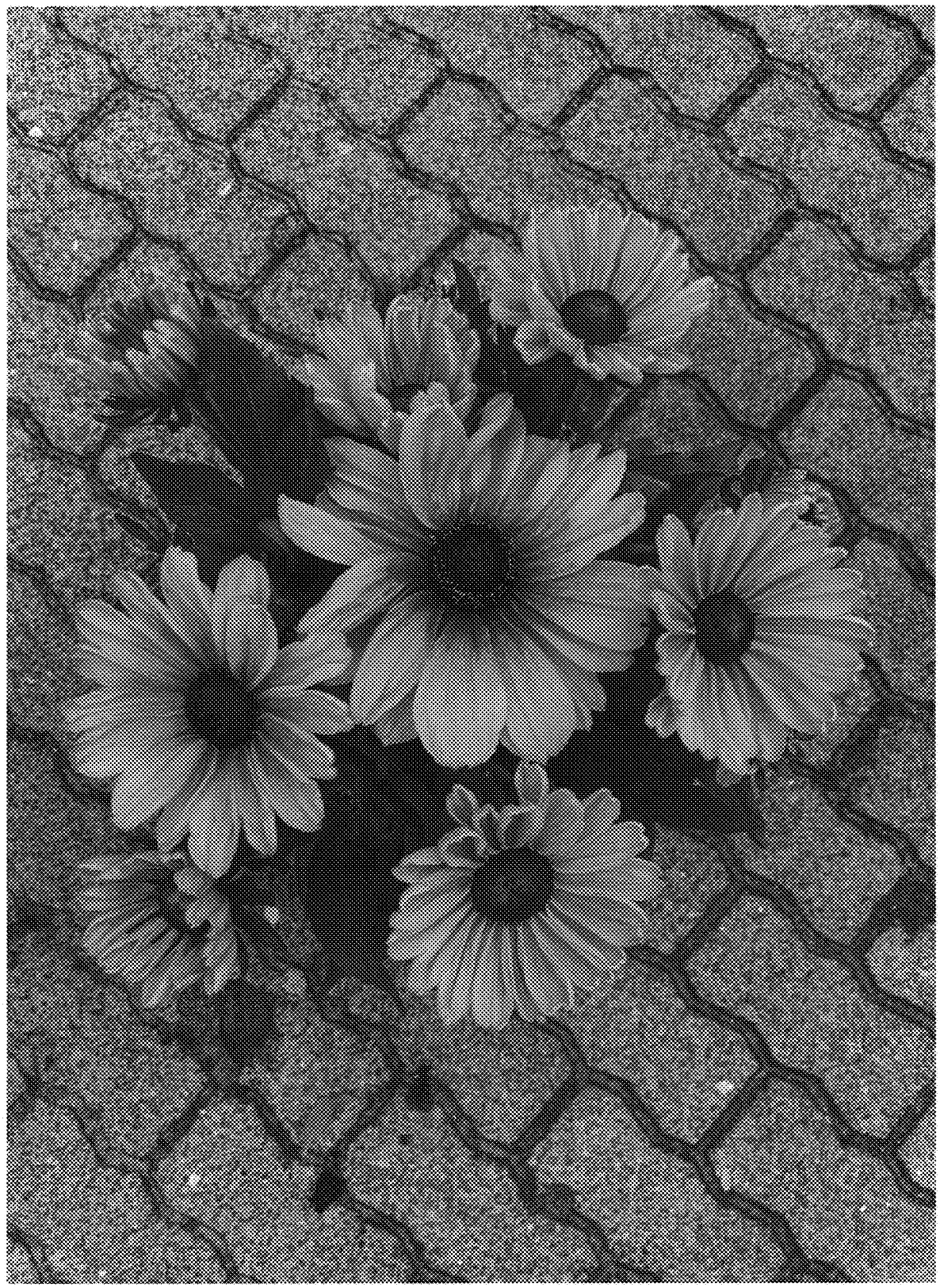
FIG. 1 shows an entire plant of the new variety.
Figure 2:
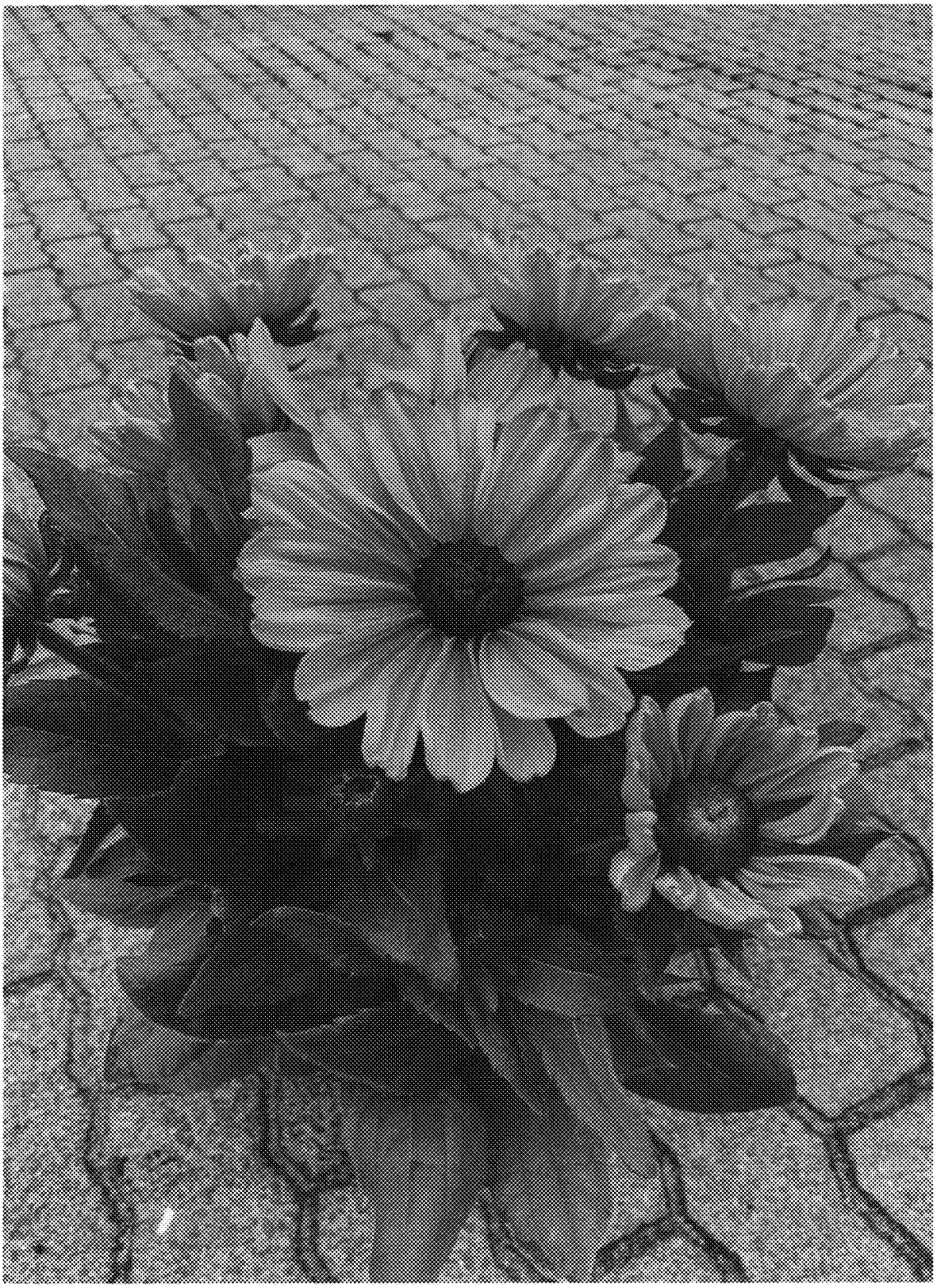
FIG. 2 shows an entire plant of the new variety.
Figure 3:
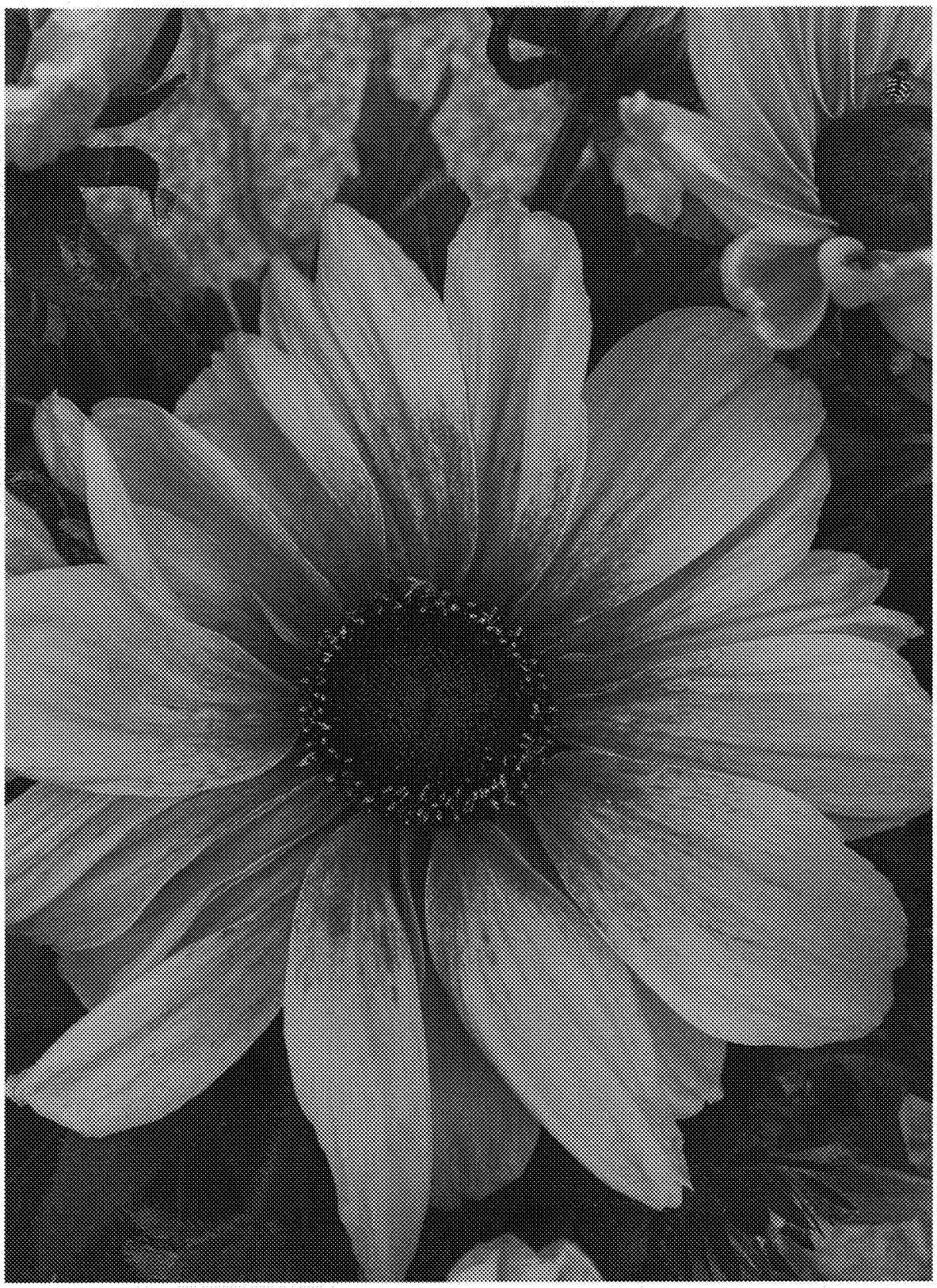
FIG. 3 shows a close-up view of the blooms of the new variety.

The following detailed description sets forth the characteristics of the new variety as the result of asexual reproductions performed via in vitro tissue culture cuttings carried out in Gönnebeck, Germany. Plants of the new variety were grown outdoors in 21 cm (4 liter) pots under normal field production conditions, and the color readings and measurements were observed outdoors under natural light on 18 week old plants in Gönnebeck, Germany. Color references are primarily to The 2015 R.H.S. Colour Chart of The Royal Horticultural Society of London, Sixth Edition, except where terms of ordinary significance are used.

Plant:

*Time to initiate roots*.—About 7-10 days at approximately 18° C.

*Time to develop roots*.—About 35-38 days at approximately 16-18° C.

*Time to produce a finished flowering plant from a rooted cutting.*—About 11-14 weeks in a 21 cm container.

*Rooting habit.*—Exhibits numerous roots of medium thickness that are freely branching and healthy in appearance.

*Plant height.*—50.0-68.0 cm.

*Plant width.*—30.0-50.0 cm.

*Vigor.*—Medium, with an upright, compact, and uniform growth habit.

*Disease/pest resistance.*—Nothing unusual noted to date.

*Temperature tolerance.*—From −3 to +40° C.

*Drought tolerance.*—Average.

*Branching habit.*—Exhibits one dominant strong branch with several lateral side branches. The lateral branches are upright, forming an attractive habit.

*Branches (flowering stems).*—Number per plant: 10-25. Length: 15.0-30.0 cm. Diameter: 5.0-10.0 mm. Internode length: 2.0-12.0 cm. Angle: Upright and outward. Strength: Strong. Texture: Pubescence present. Color: Close to Yellow-Green Group RHS 144A.

*Foliage.*—Arrangement: Single. Leaf: Length: 5.0-23.0 cm. Width: 1.5-12.0 cm. Shape: Oblanceolate. Apex: Acuminate. Base: Attenuate to acute. Margin: Dentate and undulate. Texture: Upper surface: Rough, with pubescence present. Lower surface: Rough, with pubescence present. Color: Young leaves: Upper surface: Close to Green Group RHS 137B. Lower surface: Close to Green Group RHS 137D. Mature leaves: Upper surface: Close to Green Group RHS 137B to 137C. Lower surface: Close to Green Group RHS 137D. Petiole: None present. Veins: Venation type: Pinnate. Color: Upper surface: Close to Yellow-Green Group RHS 145C. Lower surface: Close to Yellow-Green Group RHS 145A.

Inflorescence:

*Bud.*—Diameter: 3.0-5.0 cm. Length: 2.0-6.0 cm. Color: Close to Yellow-Green Group RHS 151A to Yellow-Orange Group RHS 17C.

*Appearance.*—Elliptic-shaped ray florets and tubular-shaped disc florets.

*Natural flowering season.*—Flowering occurs from June-October in Gönnebeck, Germany, beginning approximately 10-12 weeks after planting.

*Average number of inflorescences per plant.*—10-30.

*Average number of inflorescences per branch.*—1-5.

*Disc and ray floret arrangement.*—Disc florets are arranged in the middle of the receptacle of the composite, single, freely flowering plant, with ray florets extending outwardly therefrom.

*Fragrance.*—Unchanging.

*Inflorescence.*—Diameter: 13.0-18.0 cm. Height (depth): 2.0-4.0 cm. Diameter of disc: 2.5-4.0 cm. Receptacle height: 1.0-1.5 cm. Receptacle diameter: 4.0-8.0 cm.

*Ray florets.*—Number per inflorescence: 12-25. Arrangement: In one or two whorls. Length: 5.0-8.0 cm. Width: 2.5-4.5 cm. Shape: Elliptical. Apex: Emarginate. Base: Acute. Margin Entire. Texture: Upper surface: Smooth and glabrous. Lower surface: Rough. Color: When opening: Upper surface: Close to Yellow-Orange Group RHS 21A. Lower surface: Close to Yellow-Orange Group RHS 15B. At maturity: Upper surface: Close to Yellow-Orange Group RHS 17A with Greyed-Orange Group RHS 175A at the base. Lower surface: Close to Yellow-Orange Group RHS 15B. Ground color description: Close to Yellow-Orange Group RHS 21A and Greyed-Orange Group RHS 175A. Venation: Appearance: Parallel. Color: Upper surface: Yellow and brown, same color as the florets. Lower surface: Yellow.

*Disc florets.*—Number per inflorescence: Numerous; too many to quantify. Arrangement: In the center of receptacle. Length: 5.0-10.0 mm. Width: About 1.0 mm. Shape: Tubular. Apex: Five-pointed. Color: Immature: Close to Brown Group RHS 200B. At maturity: Close to Brown Group RHS 200A.

*Phyllaries.*—Number per inflorescence: 30-40. Arrangement: In three whorls. Length: 1.0-3.0 cm. Width: 3.0-8.0 mm. Shape: Lanceolate. Apex: Elongated oval. Base: Fused. Margin: Undulate. Texture: Upper surface: Rough, with pubescence present. Lower surface: Rough, with pubescence present. Color: Immature: Upper surface: Close to Green Group RHS 138A. Lower surface: Close to Green Group RHS 138B. At maturity: Upper surface: Close to Green Group RHS 138A. Lower surface: Close to Green Group RHS 138B.

*Reproductive organs.*—

*Androecium.*—Presence: On disc florets. Number (per floret): Numerous. Filament color: Close to Brown Group RHS 200A. Anther: Shape: Oval. Length: 1.0 mm. Color: Close to Brown Group RHS 200A. Pollen: Color: Close to Yellow-Orange Group RHS 15A. Amount: Plentiful — too much to quantify.

*Gynoecium.*—Presence: In disc florets. Pistil length: About 2.0 mm. Stigma: Shape: Two-parted. Color: Close to Brown Group RHS 200A. Style: Length: 1.0-2.0 mm. Color: Close to Brown Group RHS 200A.

*Seeds.*—Overall size: Approximately 2.0 mm. Color: Approximately Black Group RHS 202A.

I claim:

1. A new and distinct variety of *Rudbeckia* plant named 'BullRudi 11', as is herein illustrated and described.

* * * * *